United States Patent
Atzeni et al.

(10) Patent No.: US 7,317,194 B2
(45) Date of Patent: *Jan. 8, 2008

(54) MICROSCOPE FOR PERFORMING MULTIPLE FREQUENCY FLUOROMETRIC MEASUREMENTS

(75) Inventors: Salvatore Atzeni, Edison, NJ (US); James Mattheis, Edison, NJ (US); Raymond Kaminski, Edison, NJ (US)

(73) Assignee: Horiba Jobin Yuon, Inc., Edison, NJ (US)

( * ) Notice: Subject to any disclaimer, the term of this patent is extended or adjusted under 35 U.S.C. 154(b) by 236 days.

This patent is subject to a terminal disclaimer.

(21) Appl. No.: 10/763,681

(22) Filed: Jan. 23, 2004

(65) Prior Publication Data

US 2004/0223152 A1   Nov. 11, 2004

(51) Int. Cl.
*G01N 21/62* (2006.01)
*G01N 21/64* (2006.01)

(52) U.S. Cl. .............. 250/458.1; 250/459.1; 356/317; 356/318

(58) Field of Classification Search ............ 250/201.3, 250/458.1, 459.1; 356/317, 318, 417
See application file for complete search history.

(56) References Cited

U.S. PATENT DOCUMENTS

| | | | | |
|---|---|---|---|---|
| 4,180,328 A | * | 12/1979 | Drain | .................. 356/487 |
| 5,196,709 A | * | 3/1993 | Berndt et al. | ............ 250/458.1 |
| 5,865,754 A | * | 2/1999 | Sevick-Muraca et al. | ... 600/476 |
| 5,981,957 A | * | 11/1999 | Cruce et al. | ............ 250/458.1 |
| 6,496,267 B1 | * | 12/2002 | Takaoka | ..................... 356/497 |
| 6,741,346 B1 | * | 5/2004 | Gerstner et al. | ........... 356/318 |
| 2002/0072677 A1 | * | 6/2002 | Sevick-Muraca et al. | ... 600/473 |
| 2003/0043384 A1 | * | 3/2003 | Hill | ........................... 356/510 |
| 2003/0067607 A1 | * | 4/2003 | Wolleschensky et al. | ... 356/484 |
| 2004/0156053 A1 | * | 8/2004 | Wolleschensky et al. | ... 356/485 |
| 2006/0022145 A1 | * | 2/2006 | McLoskey et al. | ...... 250/458.1 |

* cited by examiner

*Primary Examiner*—Georgia Epps
*Assistant Examiner*—Brian J Livedalen
(74) *Attorney, Agent, or Firm*—Anthony H. Handal; Brown, Rudnick, Berlack & Israels, LLP.

(57) ABSTRACT

An optical imager, such as a microscope for performing multiple frequency fluorometric measurements comprising a light source, such as a laser source is disclosed. The system is used to excite a sample into the fluorescent state. Light from the excited sample is collected by a microscope. The microscope utilizes conventional confocal optics optimized to have a very narrow depth of field, thus limiting the information collected to a thin planar region. Measurements are taken over the fluorescence lifetime of the sample simultaneously from the excitation source and from the excited sample. Information is taken in a matrix and comparison of the image matrix and the standard during simultaneous measurements yields output information.

29 Claims, 6 Drawing Sheets

MICROSCOPE FOR PERFORMING MULTIPLE FREQUENCY FLUOROMETRIC MEASUREMENTS

TECHNICAL FIELD

The present invention relates to the field of fluorometric and phosphorescence measurement using light modulated in intensity with a plurality of frequencies.

BACKGROUND

The characteristics of light emanating from an object or a sample may be advantageously detected in order to determine characteristics of the emission source. For many years, spectrographic techniques have been used to perform analysis of materials ranging from human blood and other biological materials to slag from a crucible. For example, it has been known that wavelengths of light absorbed by a material, as well as the wavelengths of light emitted by a material during an excited state, such as combustion, both indicate the composition of the material. Today, analytic instruments in industrial, scientific and medical applications make widespread use of such emission spectra and absorption spectra. Other techniques for exciting molecules to emit light include formation of a plasma. Causing light to fall upon a material to be analyzed may also be used to stimulate emission of light for spectrographic analysis. Such techniques include Raman spectroscopy, where, for example, the output of a mercury vapor arc may be filtered and used to excite a transparent sample. As the light passes to the sample, it is scattered and undergoes a change in wavelength and a random alteration in phase due to changes in rotational or vibrational energy of the scattering molecules. Raman scattering is a principal analytic tool in industry and science today.

Another class of analytic instruments uses fluorescence measurements to identify materials. In such systems, an excitation source, such as a laser, is used to excite atoms or molecules, raising electrons into higher energy states. When the electrons revert back to the unexcited state, they fluoresce or emit photons of light characteristic of the excited atom or molecule. The wavelength of the emitted light thus contains information respecting the identity of the excited atom or molecule. In addition, the delay between the exciting light and the emitted light, as well as the amplitude of the emitted light, both give information respecting the excited atom or molecule.

While one may visualize an excitation pulse of light being pumped into a sample and the emission spectra measured and analyzed over time, in practice, such measurements are achieved by causing a light source from an excitation source modulated with a radio frequency periodic signal to excite a sample. In particular, a pulsed dye laser, or a continuous wave laser whose output is modulated by a Pockels cell, may be used to excite a sample to fluoresce. In such systems, the modulated laser excitation source is caused to fall on the sample. The modulated laser excitation source comprises a pencil of light modulated in intensity at the laser intensity modulation frequency. After a very short period of time, the system reaches the steady-state. During the steady-state, a steady-state fluorescence emission occurs. This steady-state fluorescence emission may be measured to determine the phase and modulation of the emission as compared to the excitation.

BRIEF SUMMARY OF THE INVENTION

By "phase" is meant the delay, for example, in degrees, of the steady-state modulated fluorescence emission signal as compared to the modulated laser excitation source. By "modulation", sometimes also referred to as the modulation ratio, is meant the ratio of the amplitude of a fixed reference sample portion of the modulated laser excitation source to the amplitude of the steady-state fluorescence emission.

In practice, modulation may be measured by comparing the amplitude of the steady-state fluorescence emission (the measurement signal) to the amplitude of a fixed portion of the modulated laser excitation source. (the reference signal) This fixed portion of the modulated laser excitation source may be extracted from the excitation source using a partially silvered mirror. In addition, phase may also be obtained by detecting and measuring the phase of the envelope of the steady-state fluorescence emission as compared to the reference signal.

Conventionally, as is illustrated, for example, in U.S. Pat. No. 4,937,457 to Mitchell, this is done by causing the steady-state fluorescence emission to fall upon a photomultiplier tube which has one of its dynodes driven by a heterodyne oscillator whose heterodyne signal output frequency differs from the frequency of the periodic signal by a relatively small difference frequency (for example, less than 500 Hz). The result, in the steady-state, is that the photomultiplier acts as a mixer, effectively multiplying the heterodyne signal by the steady-state fluorescence emission and generating a modulation product at the relatively small difference frequency. The amplitude and phase of the modulation product, which functions as a measurement signal, may then be used to determine the desired modulation and phase information.

In order to determine the amplitude and phase of the modulation product, it is necessary to measure the same against a reference. A fixed portion of the modulated laser excitation source may be used as a reference. In particular, the fixed portion of the modulated laser excitation source, which was extracted from the excitation source using a partially silvered mirror, is sent to a second photomultiplier tube. The second photomultiplier tube also has one of its dynodes driven by the same heterodyne oscillator. Accordingly, the second photomultiplier tube also acts as a mixer and outputs a reference modulation product at the same relatively small difference frequency. The amplitude and phase of the reference modulation product may then be used as a standard to determine the relative modulation and phase of the measurement signal.

Extraction of modulation and phase information may be done digitally.

A further refinement in the measurement technique is to perform the above measurement of modulation and phase on a sample many times using different modulation frequencies each time. Generally, this will result in the generation of a first characteristic for phase as a function of modulating frequency and a second characteristic for modulation which may also be plotted against frequency. Generally, phase angle will increase for increasing laser intensity modulation frequency. Moreover, for samples exhibiting longer lifetimes, phase differences will be larger at a given frequency of modulation.

Similarly, modulation tends to decrease in amplitude with increasing laser intensity modulation frequency.

Moreover, for samples exhibiting longer lifetimes, modulation tends to a lower value. This is so because the statistical probability of emission of a longer-lived state is spread over a longer period of time.

If curve fitting techniques are used to match the plot of frequency versus phase and the plot of frequency versus modulation, to a pair of equations, analysis of the equations can be used to discern multiple individual fluorescing components, for example organic molecules, fluorescing semiconductor depositions or dopants or the like, in a sample.

Curve fitting techniques are known in the field today and generally involve the use of a digital computer to perform the desired curve fitting and the comparison of various physical models that represent the molecular system and its environment.

Presently, it is possible to measure such features as rotation of molecules of a sample using polarized light, electrical fields, or the like. For example, if a molecule is rotating in a liquid, on account of Brownian motion or other influence, binding of an agent to a molecule will make the molecule heavier and may also affect its viscous resistance. This would translate into changes in rotation rate as a result of changes in the molecular size, shape and hydrodynamic volume.

In accordance with the invention, it has been recognized that the identification of multiple components in certain types of samples can be facilitated through the association of spatial data with optical readings. This may be achieved through the use of a fluorescence detector having a plurality of elements. In accordance with the invention, different points on a sample produce fluorescence emissions which are measured by separate fluorescence detector elements. Accordingly, it is possible to measure a particular effect with respect to different parts of the sample.

More particularly, in accordance with the invention, a light source, such as a laser source, is used to excite a sample into the fluorescent state. Light from the excited sample is collected by a microscope. The microscope utilizes conventional confocal optics optimized to have a very narrow depth of field, thus limiting the information collected to a thin planar region.

It will be understood to those of skill in the art that a microscope is only one way to get image (spatial) data. The inventive system may be employed in connection with any suitable image generation system.

In accordance with the invention, an image in two dimensions of this planar region is focused on the sensitive input face of an image intensifier. The image intensifier, at its output, presents an amplified optical image of the thin planar region. This amplified optical image then drives, for example, two dimensional array detector such as CCD (charge-coupled device), CMOS array, or other array detectors.

The CCD array detector outputs a two-dimensional matrix of information respecting the fluorescence characteristics of the various parts of the sample. In accordance with the invention it is contemplated that various excitation wavelengths will be used to cause fluorescence, and that various types of filters may be used in connection with the output fluorescence information. For example, a band reject filter may be used to eliminate the excitation wavelengths. A high pass, low pass or bandpass optical filter may also be used to reduce noise by passing fluorescence wavelengths of interest.

If the sample is a slide supporting a sample of biological material, such as a plurality of cells in a liquid medium, as detailed below, depending upon magnification and other parameters, the matrix of information comprises a picture of the fluorescence characteristics of various parts of the cell.

For example, if a mammary gland cell is in being imaged, and the cell is being treated with a drug, the matrix of information may show that the drug is entering the cell through the cell membrane at a particular rate. Likewise, after a time the matrix of information may reflect absorption of the drug by the Golgi apparatus but not in the rough endoplasmic reticulum. Such features may be geographically illustrated or numerically analyzed.

Likewise, if the drug is undergoing molecular bonding (as opposed to just being present) in a particular region of the cell, this may be measurable by fluorescence measurements with appropriate sources and filters.

In accordance with the present invention, it is contemplated that fluorescence information can be graphically displayed. For example, depending upon amplitude, each part of the image may be color-coded for intensity, for example on a scale wherein violet is indicative of the highest energy level, blue is indicative of the next highest energy level, green indicative of a still lower energy level and so forth through the spectrum to the color red which is indicative of the lowest energy level.

It is important to note that, the information obtainable is not limited to amplitudes but also the lifetime of desired parameters in model space, which can be graphically displayed as two-dimensional or three-dimensional data. Such an energy level display may be useful standing alone. However, the display may have superimposed on the energy level display a graphical indication of the parts of the image. Such a graphical indication may be generated by simple image display or may be enhanced using artificial intelligence or other computer techniques, such as boundary detection and other well-known imaging techniques. Such information can be sent to an imaging device and the imaging information superimposed on the matrix of information.

Using such techniques, and computer implemented pattern analysis techniques, rotation may be measured. Moreover, because such measurement is based on image data, such rotation information can be generated in greater detail than that obtainable using conventional techniques.

BRIEF DESCRIPTION OF THE DRAWINGS

The advantages, and the method and apparatus of the present invention will be understood from the following description taken together with the drawings, in which.

DETAILED DESCRIPTION OF THE BEST MODE OF THE INVENTION

Figure 1:
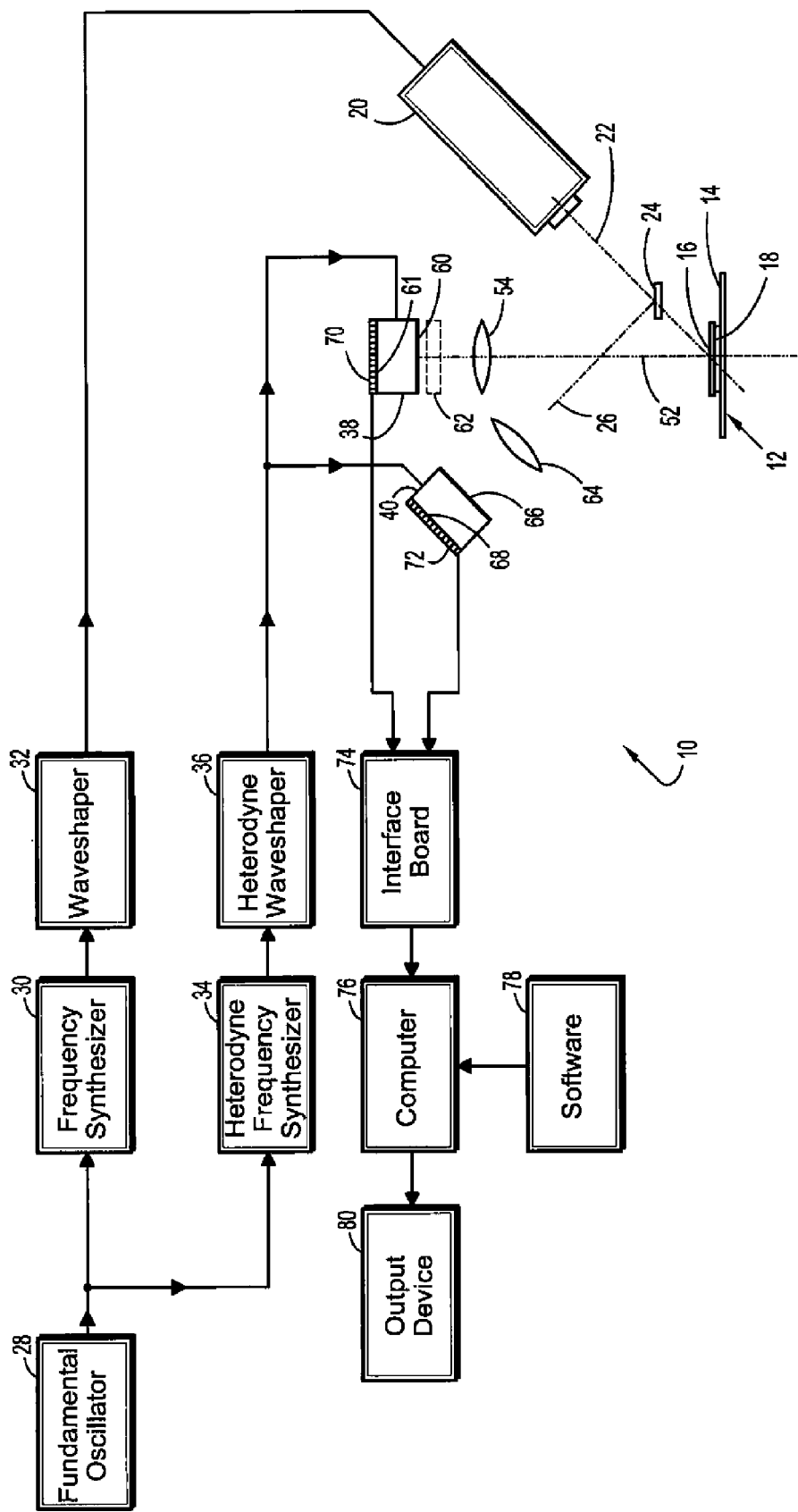
FIG. 1 is a block diagram of a system for implementing the method of the present invention.

Referring to FIG. 1, a fluorescence microscope system 10, illustrative of an example of an inventive luminescence image generating system, constructed in accordance with the present invention is illustrated. In particular, a slide 12 comprises a glass slide base 14 and a glass cover 16. Sample 18, which may be liquid, or a solid or dry material, is positioned between glass slide base 14 and glass cover 16.

Figure 2:
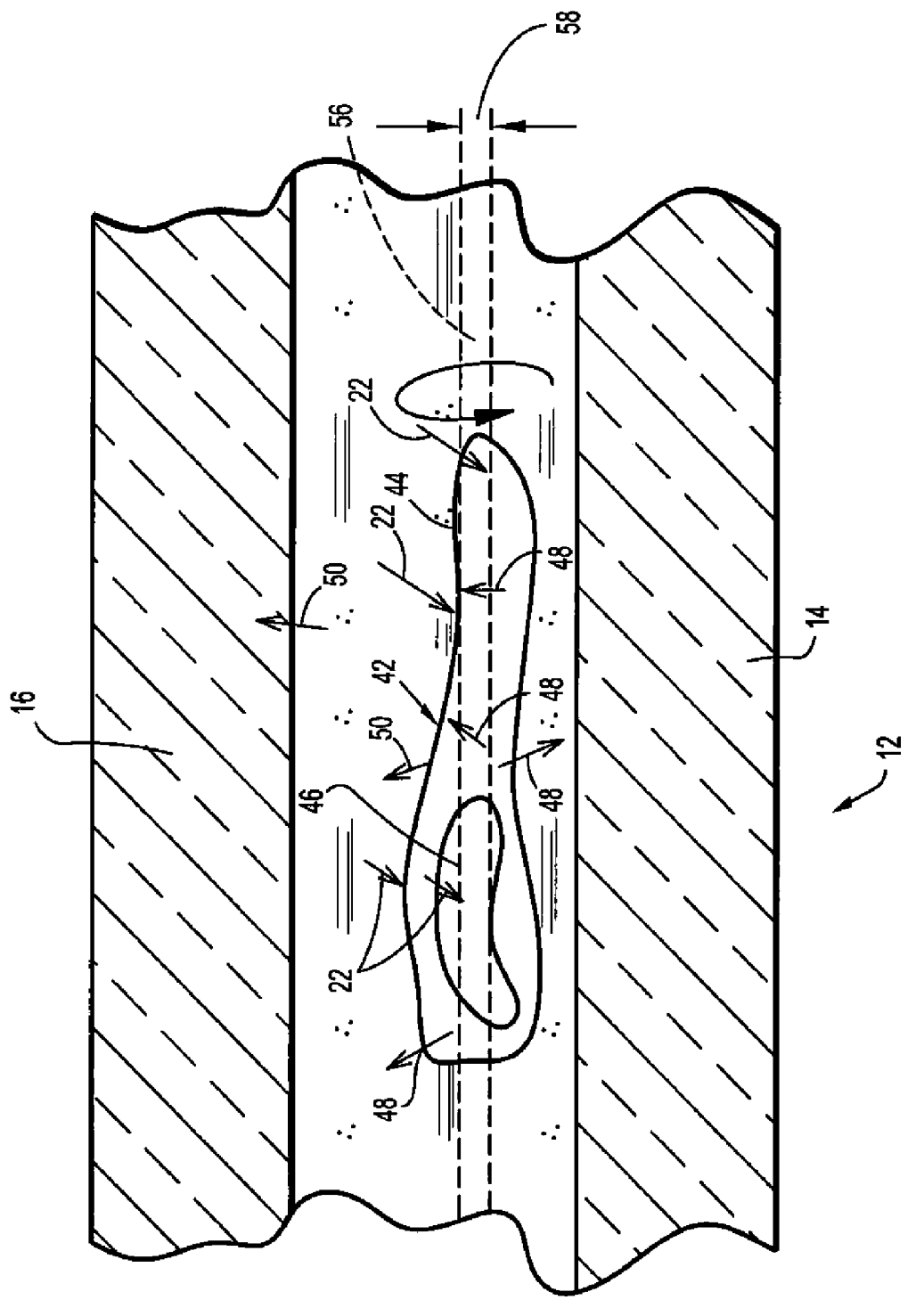
FIG. 2 is a detail showing a sample under observation by the inventive system.

Sample 18 is illuminated by a source of light such as laser 20, which outputs a pencil beam 22 of light which falls on sample 18 as illustrated in FIG. 2. Beam 22 passes through a half-silvered mirror 24. Half-silvered mirror 24 has the characteristic of reflecting only a very small portion of beam 22. In accordance with the preferred embodiment of the invention, half-silvered mirror 24 reflects only as much of beam 22 as is necessary to generate a clear signal for use as a reference beam 26, as will be described below. Depending upon the nature of the reference signal detector optics and detector electronics, half-silvered mirror 22 may reflect as little as two or three percent of beam 22. It is desirable to minimize the percentage of beam 22 which is diverted away from sample 18 to form reference beam 26, in order that the maximum amount of energy from beam 22 falls on sample 18 and, accordingly, the maximum amount of fluorescence radiation is produced for detection by the system.

As noted above, the inventive system relies upon the demodulation of a modulated fluorescence signal stimulated by a modulated excitation light source. The same is achieved through the use of a fundamental oscillator 28 operating at the desired modulation frequency, typically in the range of 5 MHz. The output of fundamental oscillator 28 is sent to a frequency synthesizer 30 which synchronizes itself with the output of fundamental oscillator 28 and generates a plurality of other frequencies. In accordance with the preferred embodiment of the invention, fundamental oscillator 28 will output a signal at 5 MHz and at multiples of 5 MHz ranging as high as 300 MHz or higher. In accordance of the present invention, however, it is contemplated that the frequencies output by frequency synthesizer 30 may have other values, as may be convenient and/or efficient to generate, and/or process as described below, provided that the desired range of modulation frequencies is covered with enough data points to perform a least squares curve fitting operation upon the data points within a desired statistical confidence interval.

In particular, in accordance with the invention, the method of least squares is used to fit a curve as close as possible to experimental data points produced by the system by minimizing the sum of the squares of the deviations of the experimental data points from the curve. In the case where the derivation of curve describing the mathematical relationship between frequency and either modulation or phase, the functional type (linear, quadratic, exponential, some of two exponentials, etc.,) is known, the method of least squares is used to determine the parameters of a general equation of that category. Other statistical methods may also be used. In addition to estimating the parameters of the equation, the system may also be used to calculate standard error and a confidence interval. In addition, the inventive system 10 may be used even where there is no particular functional type that can be postulated as a starting point for the calculation. In such a case, standard fitting procedures may be used to gain insight into the subject matter under study. In addition, qualitative information respecting physical processes, for example as they vary over time, may be more easily understood after performance of a method of least squares approximation.

The shape and duration of the electrical pulses output by frequency synthesizer 30 may be adjusted by waveshaper 32, which operates by conventional means. Waveshaper 32 is driven by frequency synthesizer 30. In accordance with the invention, the output of waveshaper 32 is adjusted to be the sum of pulses of electrical energy at the fundamental and other frequency synthesizer frequencies.

The pulses of energy at the fundamental frequency comprise a first laser drive signal. The pulses of energy at the next highest frequency comprise a second laser drive signal. The pulses of electrical energy at the third highest frequency comprise a third laser drive signal, and so on through the range of frequencies output by frequency synthesizer 30.

The output of waveshaper 32 is sent to laser 20 which emits laser energy with a desired optical wavelength, but modulated in intensity by the output of waveshaper 32, which constitutes the summed pulses at the various frequencies generated by frequency synthesizer 30.

In accordance with the preferred embodiment of the invention, it is contemplated that the output of frequency synthesizer 30 will take the form of a plurality of electrical output signals. Each of these electrical output signals is individually shaped. All of the electrical output signals are summed to achieve the desired drive signal for laser 20.

A heterodyne frequency synthesizer 34 is synchronized to the output of fundamental oscillator 28 and outputs a plurality of heterodyne signals. There is a heterodyne signal associated with each of the output signals generated by frequency synthesizer 30. The frequency of each of these heterodyne signals is slightly different from the frequency of its associated laser drive signal. The construction of heterodyne frequency synthesizer 34 is conventional and similar to that of frequency synthesizer 30.

This difference in modulating frequencies must be different for each associated laser drive signal and its respective heterodyne signal, so that digital filters may individually separate modulation products for each of the laser drive signals at their respective frequencies. Thus, the first pair may comprise an output signal at 5 MHz and an associated heterdyne signal at 5.000005 MHz. The second pair would be 10 MHz and 10,000010 Mhz, and so forth.

This difference may be, for example, 5 Hz for the first laser drive signal, 10 Hz for the second laser drive signal, 15 Hz for the third laser drive signal, and so forth. The various heterodyne frequency signals are then coupled to a heterodyne waveshaper 36 which forms output pulses having a desired shape, duration and delay.

In accordance of the preferred embodiment of the invention, the shape of the output from heterodyne waveshaper 36 comprises the sum of the various heterodyne frequency signals.

It is noted that, in accordance in the invention, a single frequency synthesizer may perform the combined function of frequency synthesizer 30 and heterodyne frequency synthesizer 34. Likewise a plurality of appropriate waveshaping circuits, each coupled to one of the outputs of the waveshaping circuits, may be used to synthesize the desired waveforms.

The output of the heterodyne waveshaper 36 is coupled to a sample image intensifier tube 38. The output of heterodyne waveshaper 36 is coupled to the reference image intensifier tube 40.

As described above, light beam 22 illuminates a sample 18 which may include, for example, a cell 42. As illustrated in FIG. 2, cell 42 includes a membrane 44 and a nucleus 46. Cell 42 is contained in a liquid medium between slide base 14 and slide cover 16. When sample 18 is illuminated by light 22 from laser 20, the molecules comprising the cell are excited and fluoresce, emitting fluorescent radiation 48. Fluorescent radiation 48 is lower in energy than excitation source light 22, and, accordingly, it is of longer wavelength. In addition, a portion of light 22 may be reflected in various directions as light 50. Light 50, because it is simply reflected light, has the same wavelength as the excitation source light 22. A portion of both fluorescent radiation 48 and reflected excitation source light 50 travels along a path 52 (FIG. 1) toward microscope focusing optics 54, shown diagrammatically as a simple convex lens. In practice, microscope focusing optics 54 comprises a plurality of lenses in a confocal configuration, and including a number of masks to achieve the desired confocal characteristic. In particular, the desired confocal characteristic achieves focusing of objects in a narrow range of focus which consists of a planar volume 56 of relatively shallow depth 58, as illustrated in FIG. 2. The object of the use of the inventive fluorescence microscope system 10 is to view a cross-section of the object, such as cell 42 under view.

Microscope focusing optics 54 focuses both fluorescent radiation 48 and reflected excitation light 50 on the sensitive face 60 of image intensifier tube 38. During the normal operation of image intensifier tube 38, the optical image stimulates the formation of an electron image which is accelerated and triggers an avalanche to form an amplified image on the output face 61 of image intensifier tube 38. If desired, because of the relatively low level of fluorescent radiation 48 from a particular sample, reflected excitation light 50 may be blocked by a band-reject filter 62.

As discussed above, fluorescent radiation 48 has an amplitude and phase characteristic which varies from that of the excitation light 22 produced by laser 20. However, in order to measure this difference, a sample of the excitation light 22 reflected by half-silvered mirror 24 as sample light 26 must be measured. Accordingly, fluorescent radiation 48 is brought by focusing optics 64 onto the sensitive face 66 of image intensifier tube 40. The image brought to sensitive face 66 is accelerated and amplified to form an image on the output face 68 of image intensifier tube 40.

It is necessary for the two amplified images on output faces 61 and 68 to be compared in order to determine modulation and phase information. This is done by providing output face 61 with a CCD detector 70, for example a 250 element by 250 element CCD or other suitable detector, preferably with a size and resolution matched to the output of image intensifier tube 38. The output of CCD 70 is thus an image of that portion of the sample focused by focusing optics 54 on sensitive face 60.

In similar fashion, output face 68 of image intensifier tube 40 is provided with a CCD detector 72, substantially identical to CCD 70. The output of CCD 72 is thus an image of that portion of the reference light traveling along path 26 and focused by focusing optics 64 on sensitive face 66 and serves as a reference with respect to which the sample image data may be compared to generate image information.

The outputs of image intensifier tubes 38 and 40 are sent to a computer interface board 74 plugged into a computer 76. Using conventional filtering techniques, interface board 74 and computer 76 (controlled by filter software 78) together separate out the amplitude and phase information for both the reference beam 26 and fluorescent radiation 48, and generate amplitude (modulation) and phase information for the fluorescent light emitted by sample 18. In addition, because this information is associated with two-dimensional spatial data in a given plane of focus, the fluorescence characteristic may be graphically shown on an output device 80 for visual or intuitive analysis and/or numerically processed with any desired criteria to achieve any desired quantitative outputs.

Before using the inventive system to perform a measurement on a sample, it is necessary to calibrate the system. This is done by first using, in place of a sample, a standard consisting of a zero lifetime scattering solution. When the instrument measures the zero lifetime scattering solution, it creates a set of normalizing phase and modulation standard values which function as a standard. These normalized phase and modulation values, obtained using the zero lifetime scattering solution standard, are compared to measured phase and modulation values created by the system when it measures the sample. The system generates the phase and modulation standard values in the same way in which it measures phase and modulation values for a sample, as will be described in detail below. The actual phase and modulation value for a particular point on the sample is the difference, respectively, between the phase and modulation values generated for the point on the sample and the phase and modulation value generated for the same point using the zero lifetime scattering solution standard.

During operation of the inventive system to measure the characteristics of a sample, laser 20 is excited to produce modulated laser light. A small portion of the modulated laser light is reflected by half-silvered mirror 24. This reflected light takes the form of light 26 which is sent through optics 64 to sensitive face 66 of image intensifier tube 40. CCD 72 then forms a reference modulated electrical signal. In the instant example of a 250 by 250 element image intensifier tube 40 driving a 250 by 250 element CCD 72, this reference modulated electrical signal takes the form of 62,500 individual reference signals, one corresponding to each element in CCD 72. All of these 62,500 individual signals each serve as a reference signal and are downloaded in a conventional manner and sent to computer 26 via interface board 74.

The bulk of the radiation produced by laser 20 passes through half-silvered mirror 24 and falls on sample 18, causing it to fluoresce with an amplitude and phase different from the modulated (or pulsed) laser output of laser 20. Fluorescence emissions 48 from sample 18 then pass through optics 54 and are imaged on sensitive face 60 of image intensifier tube 38. Band reject filter 62 may have the characteristic of reflecting light at the output wavelength of laser 20. Accordingly, band reject filter 62 passes fluorescence emissions while blocking transmission of reflected light at the wavelength of laser 20 and preventing it from overloading image intensifier tube 38. Alternatively other filters, such as high pass filters, low pass filters or bandpass filters may be used, and, depending upon the particular measurement being performed, any one or more of these filters may provide a most nearly optimum characteristic for the detection of the fluorescence wavelengths of interest while at the same time minimizing the interference of noise in the inventive system.

Figure 3:
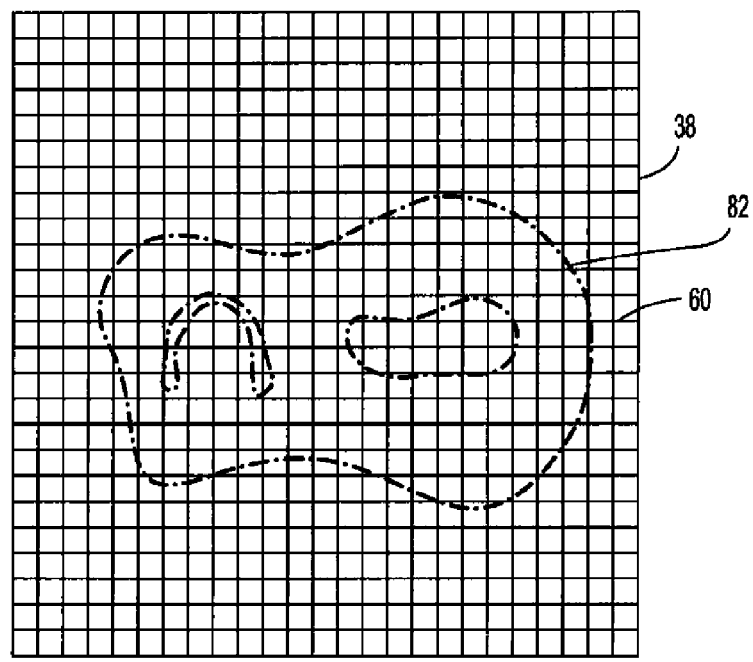
FIG. 3 illustrates a fluorescent image.
Figure 4:
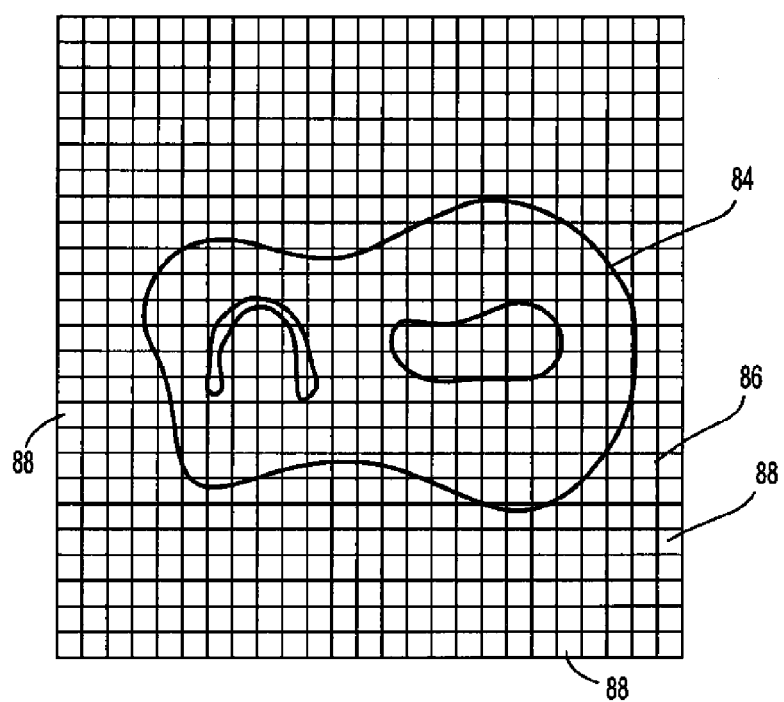
FIG. 4 illustrates an intensified fluorescence lifetime spatially resolved fluorescent image resulting in the ability to gather spatial and multi-frequency data simultaneously.

This fluorescent light takes the form of fluorescent light 48, emitted by sample 18 when it fluoresces, and is focused as an image 82 (FIG. 3) by optics 54 onto sensitive face 60 of image intensifier tube 38. It is noted that in the figures, the illustrated number of elements of image intensifier tube 38 and CCD 70 is greatly reduced for purposes of clarity of illustration. Image 82 is accelerated and intensified by image intensifier tube 38 to form an intensified lifetime based fluorescence image 84, as illustrated in FIG. 4.

Intensified image 84 then falls on the front face 86 of CCD 70. CCD 70 then forms a measurement modulated electrical signal. In the instant example of a 250 by 250 element image intensifier tube 38 driving a 250 by 250 element CCD 70, this reference modulated electrical signal takes the form of 62,500 individual measurement signals, one corresponding to each element in CCD 70. Each of the 62,500 individual measurement signals is associated with one of the 62,500 individual reference signals output from CCD 72. These 62,500 individual signals each serve as a reference signal and are downloaded in a conventional manner and sent to computer 26 via an interface board 74.

In accordance with the preferred embodiment of the invention, each one of the 62,500 individual multifrequency measurement signals (for example, each containing a hundred single frequency signals, corresponding to a hundred excitation frequency modulation components associated with each pixel 88) is compared to its respective one of the 62,500 individual reference signals to generate phase and modulation information for the point on the image associated with the particular individual measurement signal and the point on sample 18 measured by the respective individual measurement signal. This is done by filtering the output of each pixel 88 to separate out the difference frequency modulation products (one hundred is the example of fifty modulation frequencies).

Figure 5:
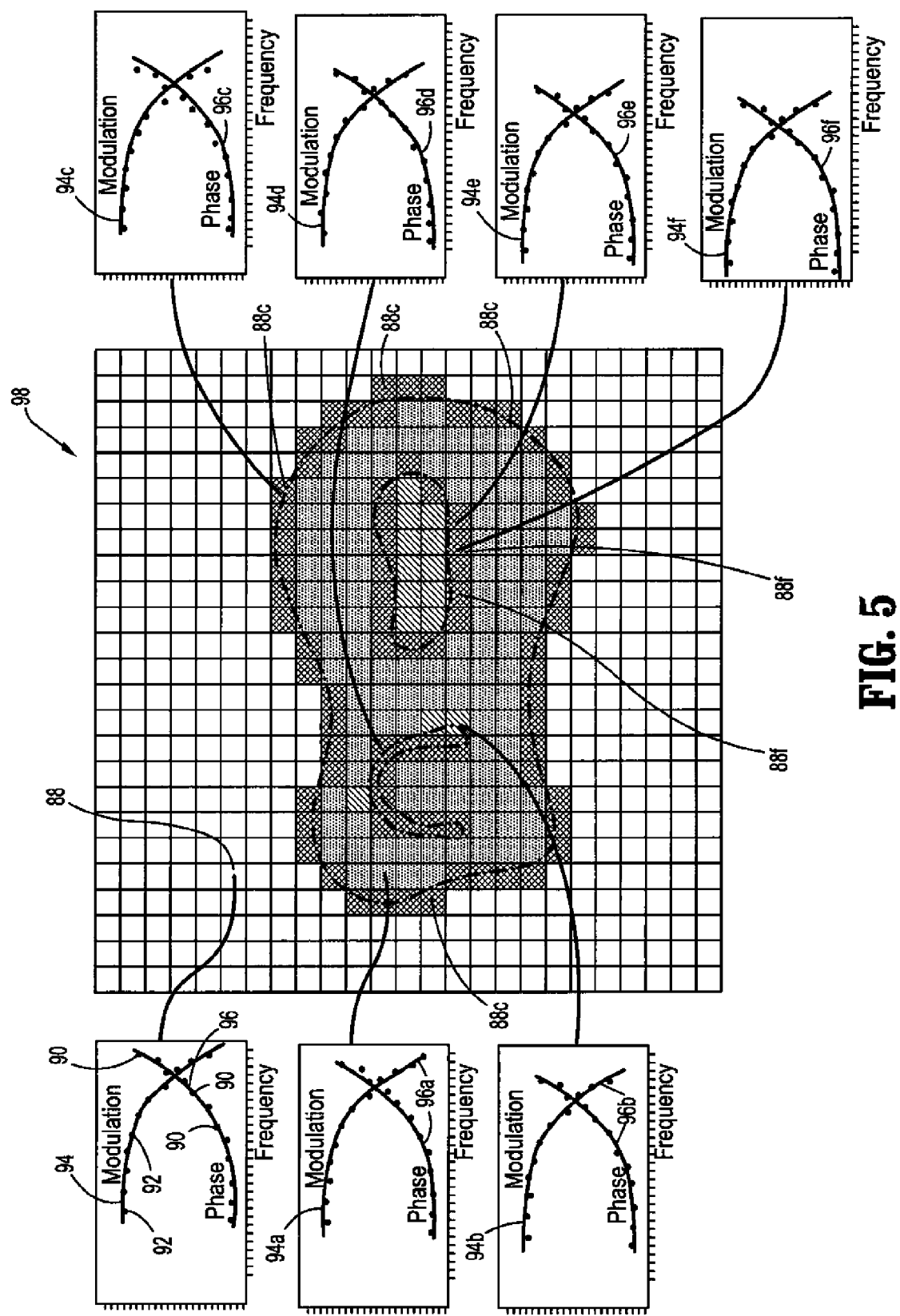
FIG. 5 illustrates an output from the inventive system together with various modulation and phase characteristics for pixels of an image which result in a particular value determination for fluorescence.

Thus, each pixel 88 generates a plurality of phase measurements 90, one for each of the excitation frequencies, as is illustrated in FIG. 5. In addition, each pixel 88 generates a plurality of modulation measurements 92 for these frequencies. This may be better understood when it is recognized that image intensifiers 38 and 40 act as mixers, mixing each of the heterodyne signals and its respective measurement signal Each one of the comparisons of respective measurement and reference signals for a particular point on sample 18 is performed individually for each of the modulation frequencies output by frequency synthesizer 30 to generate a pair of data points 92 (fifty in each pixel) In particular, there are modulation data points 92 (fifty for each pixel) and phase data points 90 (fifty for each pixel) for each of the fifty frequencies which is modulating the output of laser 20, as is illustrated in FIG. 5. Thus, as in the example above, if there are fifty different modulation frequencies used to modulate laser 20, each data measurement results in the generation of fifty modulation and fifty phase data points for each of the 62,500 individual measurement signals, or 6,250,000 data points for each interval of time over which a measurement is taken. Again, for purposes of illustration, the number of data points 90 and 92 illustrated in FIG. 5 has been reduced for purposes of clarity of illustration.

Generally, the duration of the interval over which the measurement is taken depends upon the intensity of the fluorescence information and the signal-to-noise ratio. Generally, as is known in the art, with high signal-to-noise ratios and fluorescent emission intensity, shorter intervals are sufficient to collect enough photons to achieve a good data point measurement.

Accordingly, intensified image 84 is turned into a plurality of modulation characteristic curves 94-94f and phase characteristic curves 96-96f. Each pixel receives a different excitation input and, accordingly, depending upon intensity and delay (that is modulation and phase), a plurality of modulation characteristics, for example, modulation characteristic curves 94, 94a, 94b, 94c, 94d, 94e, and 94f may be derived by computer 76. Likewise, a plurality of phase characteristics, for example, phase characteristic curves 96, 96a, 96b, 96c, 96d, 96e, and 96f, respectively, are also generated by computer 76. These phase and modulation characteristic curves correspond, respectively, to pixels 88, 88a, 88b, 88c, 88d, 88e, and 88f, and are illustrative of the calculations for the entire display.

For purposes of illustration, FIG. 5 is simplified to show a display 98 which shows calculation details for only a limited number of pixels and only seven different fluorescent lifetimes, with the shortest lifetime reflected by phase characteristic curve 96 and modulation characteristic curve 94. Characteristic curves 94a and 96a correspond to the next longest lifetime, of those illustrated. Characteristic curves 94b and 96b, 94c and 96c, 94d and 96d, 94e and 96e, and 94f and 96f, respectively, represent experimental data points for increasingly longer lifetimes.

If desired, display 98 may be color-coded or coded in shades of gray or otherwise, as illustrated in FIG. 5 to show different lifetimes with different graphical representations. These lifetimes may correspond to differences in physical characteristics. For example, in the image of cell 42, the cell wall tends to have a lifetime which may be derived from curves 94c and 96c and accordingly the display 98 includes a corresponding pixel 88c of identifiable characteristic appearance on display 98. Likewise, most of the edge of the nucleus is defined by pixels with the same measured lifetime as pixel 88f and is illustrated with a second characteristic appearance.

As may be understood from the above discussion, the inventive system results in a relatively high need for computing power. However it is unnecessary that all of this computing power be concentrated in the general purpose, and thus more expensive, mainframe of computer 76, which may be a personal computer, or a more powerful system. In particular, the number of data points and the speed with which the same may be generated and processed for a given amount of computing power may be maximized by providing interface board 74 with storage and/or calculation functions in order to reduce the computational load on the accumulator of computer 76. The result is a significant increase in speed and/or data density.

Computer 76 then processes the measurement data points in a conventional manner, for example, using them to identify particular components and concentrations of those components.

While this system has been illustrated showing a cell, semiconductor or other type of system may also be imaged and measured.

Figure 6:
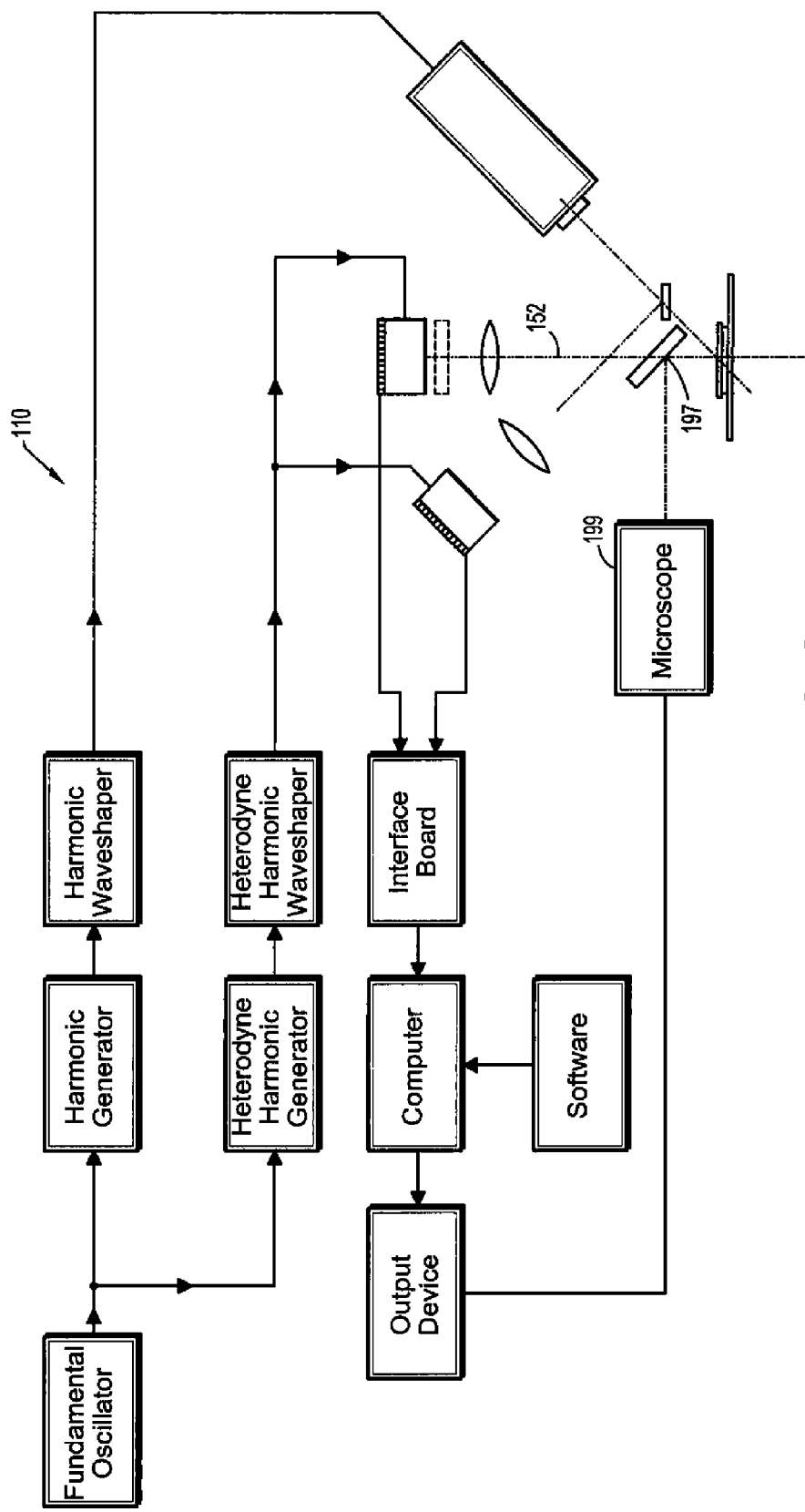
FIG. 6 is an alternative embodiment of a system for implementing the method of the present invention.

A second embodiment of the invention is illustrated in FIG. 6. In this embodiment, corresponding or analogous parts are numbered with numerals 100 higher than their corresponding parts in the FIG. 1 embodiment for purposes of succinct description in this specification. In particular, it is noted that the inventive system 110 illustrated in FIG. 6 is substantially identical to the system illustrated in FIG. 1, except for the introduction of a half-silvered mirror 197 which reflects about 5 percent of the radiation to an optical microscope 199, which may be viewed by the human eye, used to make a photographic exposure, or any other desired output. This is of particular value if a relatively low power computer is used, or a great number of data points are being acquired, as real-time adjustment of the system can be done initially using microscope 199. Alternatively, it is noted that half-silvered mirror 197 may be made completely reflective, provided that it is provided with a mounting which slides it into optical path 152, when it is being used, and removes it completely from path 152, when its use is not needed.

Figure 7:
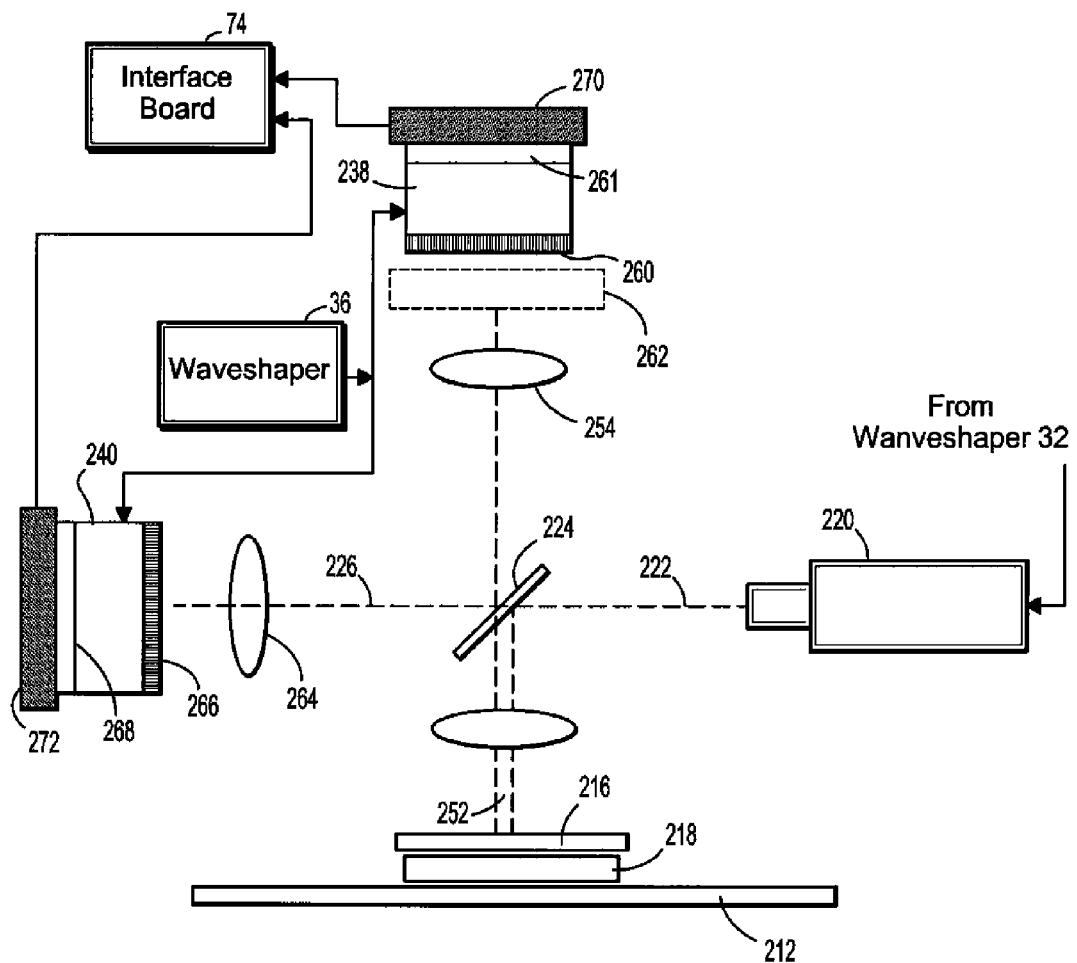
FIG. 7 is an alternative embodiment of an optical arrangement useful in, for example, the systems for implementing the method of the present invention illustrated in FIGS. 1 and 6.

A particularly advantageous optical arrangement for an optical system to be employed, for example in either the system of FIG. 1 or the system of FIG. 6, is illustrated in FIG. 7. In this embodiment, system elements corresponding to the elements of FIG. 1 are numbered 200 higher and perform substantially the same function, except that light from source 220 is reflected by half-silvered mirror 224 onto sample 218, and fluorescence radiation is passed by mirror 224 to collection optics 254 and the detector which it images. This arrangement has the advantage of maximizing the fluorescence signal compared to other light in the system, on account of the angular relationship between the optical members, excitation source and sample.

While illustrative embodiments of the invention have been described, it is understood that various modifications may be obvious to those of ordinary skill in the art. Such modifications are within the spirit and scope of the invention, which is limited and defined only by the appended claims.

The invention claimed is:

1. A method of spectrographic measurement, comprising:
   (a) generating light energy using an excitation source, said light energy being caused to fall on a sample to be assayed, causing said sample to output an output optical signal;
   (b) generating a plurality of modulation frequencies;
   (c) generating a plurality of heterodyne frequencies to form a set of heterodyne signals at said heterodyne frequencies, each of said heterodyne frequencies being associated with one of said modulation frequencies;
   (d) coupling said modulation frequencies to said excitation source, causing said excitation source to generate excitation energy modulated in intensity in proportion to said modulation frequencies;
   (e) sampling a portion of said excitation energy to form a reference excitation signal;
   (f) focusing said output optical signal as an image modulated with said plurality of modulation frequencies on an image intensifier;
   (g) intensifying said image to form an intensified image modulated with said plurality of modulation frequencies;
   (h) receiving said intensified image modulated with said plurality of modulation frequencies on a multielement optical detector;
   (i) generating a plurality of measurement signals using said multielement optical detector, each measurement signal associated with a single one of said elements;
   (j) for each measurement signal associated with a single one of said elements of said multielement optical detector, mixing said measurement signal with its respective one of said heterodyne signals to generate a plurality of low-frequency measurement modulation products, one low-frequency measurement modulation product being associated with each of said modulation frequencies and comprising the difference between a single modulation frequency and its associated heterodyne frequency and having a measurement amplitude and phase;
   (k) mixing said reference excitation energy with its respective one of said heterodyne signals to generate a plurality of reference modulation products, one reference modulation product being associated with each of said modulation frequencies and comprising the difference between a single modulation frequency and its associated heterodyne frequency and having a reference amplitude and phase, each reference modulation product being associated with one of said measurement modulation products; and
   (l) for each of said plurality of low-frequency measurement modulation products, comparing said low-frequency measurement modulation product to its associated low-frequency reference modulation product to generate an output signal indicating characteristics of said sample at the region on said sample associated with each of said elements.

2. The method of claim 1, wherein said output signal is numerically processed to generate changes over time.

3. The method of claim 1, wherein said output signal may be graphically displayed.

4. The method of claim 1, wherein said output signal is numerically processed to generate a desired parameter.

5. The method of claim 1, wherein said excitation source is a laser.

6. The method of claim 1, wherein said output optical signal comprises fluorescent energy from said sample.

7. The method as in claim 1, wherein said modulation frequencies are harmonically related.

8. The method as in claim 1, wherein excitation source is a laser whose output is modulated by a Pockel's cell.

9. The method as in claim 1, wherein said excitation source is a laser whose output is a pulsed laser.

10. The method as in claim 9, wherein said laser is a pulsed-dye laser.

11. The method as in claim 1, wherein said excitation source is a light emitting diode.

12. The method as in claim 1, wherein reference modulation products are the low-frequency reference modulation products output during said mixing operation.

13. The method as in claim 1, wherein said comparison is done by measuring the relative phase and amplitude of said low-frequency measurement modulation product as compared to said low-frequency reference modulation product and generating a modulation data point and a phase data point.

14. The method as in claim 13, further comprising:
   (m) for each element, fitting said modulation data points to a first curve using the method of least squares;
   (n) for each element fitting said phase data points to a second curve using mathematical fitting technique;
   (o) comparing said first and second curves to a database to determine characteristics of said sample; and
   (p) displaying said characteristics.

15. The method of claim 1, wherein before said excitation energy output by said excitation source is caused to fall on said sample to be measured, and the system is calibrated by first using, in place of said sample, a standard consisting of a zero lifetime scattering solution to create a set of normalizing phase and modulation standard values against which said phase and modulation values for said sample our measured.

16. A method of spectrographic measurement, comprising the steps of:
   (a) generating light energy using an excitation source, said light energy being caused to fall on a sample to be assayed, causing said sample to output an output optical signal;
   (b) generating a plurality of modulation frequencies;
   (c) generating a plurality of heterodyne frequencies to form a set of heterodyne signals at said heterodyne frequencies, each of said heterodyne frequencies being associated with one of said modulation frequencies;
   (d) coupling said modulation frequencies to said excitation source, causing said excitation source to generate excitation energy modulated in intensity in proportion to said modulation frequencies;
   (e) sampling a portion of said laser excitation energy to form a reference laser excitation signal;
   (f) focusing said output optical signal as an image modulated with said plurality of modulation frequencies on an image intensifier;
   (g) intensifying said image to form an intensified image modulated with said plurality of modulation frequencies;
   (h) receiving said intensified image modulated with said plurality of modulation frequencies on a multielement optical detector;

(i) generating a plurality of measurement signals using said multielement optical detector, each measurement signal associated with a single one of said elements; and (j) for each measurement signal associated with a single one of said elements of said multielement optical detector, comparing the output of said elements to a standard to generate an output signal indicating characteristics of said sample at the region on said sample associated with each of said elements.

17. An apparatus for performing fluorescence measurement, comprising:

(a) a light source generating laser excitation energy, oriented to illuminate a sample to be measured and cause said sample to emit fluorescent energy;

(b) a frequency generator generating a plurality of modulation frequencies and a plurality of heterodyne frequencies, each of said heterodyne frequencies being associated with one of said modulation frequencies said frequency generator being coupled to said excitation source, whereby said source generates excitation energy modulated in intensity in proportion to said modulation frequencies;

(c) an optical member positioned to receive said laser excitation energy and divert a portion of said laser excitation energy, said portion of said laser excitation energy forming a reference laser excitation signal;

(d) focusing optics positioned to receive said fluorescent energy and form an image modulated with said plurality of modulation frequencies;

(e) an image intensifier positioned to receive said image, said image intensifier having an output for outputting an intensified image modulated with said plurality of modulation frequencies;

(f) a multielement optical detector positioned to receive said intensified image modulated with said plurality of modulation frequencies and generating in response thereto a plurality of measurement signals, each associated with a single one of said elements;

(g) a mixer coupled to receive each of said measurement signals and each of said heterodyne frequencies and producing in response to said measurement signals and said heterodyne frequencies a plurality of low-frequency measurement modulation products, one low-frequency measurement modulation product being associated with each of said modulation frequencies and comprising the difference between a single modulation frequency and its associated heterodyne frequency and having a measurement amplitude and phase; and (h) a mixer coupled to said reference laser excitation signals and said heterodyne signals to generate a plurality of low-frequency reference modulation products, one low-frequency reference modulation product being associated with each of said modulation frequencies and comprising the difference between a single modulation frequency and its associated heterodyne frequency and having a reference amplitude and phase, each of said low-frequency reference modulation products being associated with one of said measurement modulation products, each of said low-frequency measurement modulation products, and their associated low-frequency reference modulation products indicating phase and modulation information.

18. The apparatus as in claim 17, wherein said optical member is a partially silvered mirror.

19. The apparatus as in claim 17, wherein said optical member is a prism.

20. An apparatus for performing fluorescence measurements, comprising:

(a) an excitation light source generating laser excitation energy;

(b) a frequency generator generating a plurality of modulation frequencies and a plurality of electrical heterodyne frequencies, each of said heterodyne frequencies being associated with one of said modulation frequencies, said frequency generator being coupled to said excitation light source, whereby said source generates modulated laser excitation energy modulated in intensity in proportion to said modulation frequencies;

(c) a first detector coupled to said heterodyne frequencies;

(d) an optical member positioned to receive said modulated laser excitation energy and cause a portion of said modulated laser excitation energy to fall on said first detector and the rest of said modulated laser excitation energy to fall on a sample to be assayed and cause said sample to emit fluorescent energy, said portion of said laser excitation energy forming a reference laser excitation signal;

(e) focusing optics positioned to receive said emitted fluorescent energy and form an image modulated with said plurality of modulation frequencies;

(f) a multielement second detector coupled to said heterodyne frequencies and positioned to receive said image, said second detector positioned to receive said image modulated with said plurality of modulation frequencies and generate in response thereto a plurality of measurement signals, each associated with a single one of said elements; and (g) a calculating device coupled to said measurement signals and said first detector, said heterodyne frequencies and said reference laser excitation signals and configured to extract phase and the modulation information.

21. The apparatus as in claim 20, wherein said calculating device is a computer.

22. The apparatus as in claim 20, wherein said focusing topics are microscope optics.

23. The apparatus as in claim 22, wherein said microscope optics are confocal optics.

24. A method of fluorescence measurement, comprising the steps of:

(a) generating light energy in the form of laser excitation energy output by an excitation source, said laser excitation energy being caused to fall on a sample to be assayed and cause said sample to emit fluorescent energy;

(b) generating a plurality of modulation frequencies;

(c) generating a plurality of heterodyne frequencies to form a set of heterodyne signals at said heterodyne frequencies, each of said heterodyne frequencies being associated with one of said modulation frequencies;

(d) coupling said modulation frequencies to said excitation source causing said source to generate excitation energy modulated in intensity in proportion to said modulation frequencies;

(e) sampling a portion of said laser excitation energy to form a reference laser excitation signal;

(f) focusing said fluorescent energy as an image modulated with said plurality of modulation frequencies on an image intensifier;

(g) intensifying said image to form an intensified image modulated with said plurality of modulation frequencies;

(h) receiving said intensified image modulated with said plurality of modulation frequencies on a multielement optical detector;

(i) generating a plurality of measurement signals using said multielement optical detector, an output signal being output from each of the elements of said multi-element optical detector, each measurement signal associated with a single one of said elements;

(j) for each measurement signal associated with a single one of said elements of said multielement optical detector, mixing said measurement signal with its respective one of said heterodyne signals to generate a plurality of low-frequency measurement modulation products, one low-frequency measurement modulation product being associated with each of said modulation frequencies and comprising the difference between a single modulation frequency and its associated heterodyne frequency and having a measurement amplitude and phase;

(k) mixing said reference laser excitation signal with its respective one of said heterodyne signals to generate a plurality of low-frequency reference modulation products, one low-frequency reference modulation product being associated with each of said modulation frequencies and comprising the difference between a single modulation frequency and its associated heterodyne frequency and having a reference amplitude and phase, each of said low-frequency reference modulation products being associated with one of said measurement modulation products;

(l) for each of said plurality of low-frequency measurement modulation products, comparing said low-frequency measurement modulation product to its associated low-frequency reference modulation product to measure the relative phase and amplitude of said low-frequency measurement modulation product as compared to said low-frequency reference modulation product and generating a modulation data point and a phase data point;

(m) for each element, fitting said modulation data points to a first curve using a mathematical fitting technique;

(n) for each element fitting said phase data points to a second curve using a mathematical fitting technique;

(o) comparing said first and second curves to a database to determine characteristics of said sample; and (p) displaying said characteristics.

25. The method of claim 24, wherein before said excitation energy output by said excitation source is caused to fall on said sample to be measured, and the system is calibrated by first using, in place of said sample, a standard consisting of a zero lifetime scattering solution to create a set of normalizing phase and modulation standard values against which said phase and modulation values for said sample are measured.

26. The method of claim 25, wherein said normalizing phase and modulation standard values are generated by the steps of:

(q) causing said generated light energy in the form of laser excitation energy output by said excitation source to fall on a zero lifetime standard, causing said sample to output a reference standard optical signal;

(r) generating a plurality of modulation frequencies;

(s) generating a plurality of heterodyne frequencies to form a set of heterodyne signals at said heterodyne frequencies, each of said heterodyne frequencies being associated with one of said modulation frequencies;

(t) coupling said modulation frequencies to said excitation source causing said source to generate excitation energy modulated in intensity in proportion to said modulation frequencies;

(u) sampling a portion of said laser excitation energy to form a reference laser excitation signal;

(v) focusing said reference standard optical signal as a standard image modulated with said plurality of modulation frequencies on said image intensifier;

(w) intensifying said standard image to form an intensified standard image modulated with said plurality of modulation frequencies;

(x) receiving said intensified standard image modulated with said plurality of modulation frequencies on said multielement optical detector;

(y) generating a plurality of measurement signals using said multielement optical detector, a signal being output from each of the elements of said multielement optical detector, each measurement signal associated with a single one of said elements;

(z) for each measurement signal associated with a single one of said elements of said multielement optical detector, mixing said measurement signal with said heterodyne signal to generate a plurality of low-frequency measurement modulation products, one low-frequency measurement modulation product being associated with each of said modulation frequencies and comprising the difference between a single modulation frequency and its associated heterodyne frequency and having a measurement amplitude and phase;

(aa) mixing said reference laser excitation signal with said heterodyne signal to generate a plurality of low-frequency reference modulation products, one low-frequency reference modulation product being associated with each of said modulation frequencies and comprising the difference between a single modulation frequency and its associated heterodyne frequency and having a reference amplitude and phase, each of said low-frequency reference modulation products being associated with one of said measurement modulation products; and (bb) for each of said plurality of low-frequency measurement modulation products, comparing said low-frequency measurement modulation product to its associated low-frequency reference modulation product to measure the relative phase and amplitude of said low-frequency measurement modulation product as compared to said low-frequency reference modulation product and generating a reference standard modulation data point and a reference standard phase data point.

27. A method of spectrographic analysis comprising (a) generating light modulated by a plurality of modulation frequencies;

(b) generating a plurality of heterodyne frequencies each associated with one of said modulation frequencies, each of said heterodyne frequencies being different from its corresponding modulation frequency;

(c) splitting the light modulated by said plurality of modulation frequencies into reference light and measurement light;

(d) causing said measurement light to fall on a sample to be assayed and to be focused as an image onto a multielement optical detector to stimulate the production of a plurality of measurement signals;

(e) sending said plurality of measurement light signals and said heterodyne frequencies to a first mixer to generate a plurality of measurement product outputs;

(f) sending said heterodyne frequencies and said reference light to a second mixer to generate a plurality of reference modulation product outputs; and (g) sending the plurality of measurement product outputs of said first mixer and the plurality of reference modulation products of said second mixer to a computer for analysis of said sample.

28. The method as in claim 27, wherein said modulation frequencies and said heterodyne frequencies are synchronized to each other.

29. The method as in claim 28, wherein said heterodyne frequencies are derived from said modulation frequencies.

* * * * *